United States Patent
Brommersma et al.

(10) Patent No.: US 6,827,717 B2
(45) Date of Patent: Dec. 7, 2004

(54) MONOPOLAR AND BIPOLAR ELECTRODE FOR A UROLOGICAL RESECTOSCOPE

(75) Inventors: Pieter Brommersma, Bargteheide (DE); Felix Nussbaum, Hamburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 245 days.

(21) Appl. No.: 10/111,196

(22) PCT Filed: Aug. 4, 2001

(86) PCT No.: PCT/EP01/09044
§ 371 (c)(1),
(2), (4) Date: Jun. 4, 2002

(87) PCT Pub. No.: WO02/17807
PCT Pub. Date: Mar. 7, 2002

(65) Prior Publication Data
US 2004/0044343 A1 Mar. 4, 2004

(30) Foreign Application Priority Data
Aug. 26, 2000 (DE) ............................. 100 42 096
Apr. 26, 2001 (DE) ...................... 201 07 176 U

(51) Int. Cl.[7] .............................................. A61B 18/18
(52) U.S. Cl. ........................................... 606/46; 606/41
(58) Field of Search ................... 606/27–29, 37–41, 606/45–50

(56) References Cited

U.S. PATENT DOCUMENTS

| 4,726,370 A | * | 2/1988 | Karasawa et al. | ............. | 606/46 |
| 4,917,621 A | | 4/1990 | Grossi et al. | | |
| 4,919,131 A | | 4/1990 | Grossi et al. | | |
| 6,565,561 B1 | * | 5/2003 | Goble et al. | .................. | 606/41 |

FOREIGN PATENT DOCUMENTS

| DE | 25 21 719 A1 | 5/1975 |
| DE | 39 17 583 A1 | 3/1990 |
| DE | 39 18 316 A1 | 3/1990 |
| FR | 2 400 351 A | 3/1979 |

OTHER PUBLICATIONS

WO 96/23449, Electro–Surgical Tissue Removal, Publication Date Aug. 8, 1996.

* cited by examiner

Primary Examiner—Rosiland Rollins
(74) Attorney, Agent, or Firm—Rankin, Hill, Porter & Clark LLP

(57) ABSTRACT

The invention relates to an electrode that can be subjected to a high frequency, the electrode including an electrode carrier having at least one external, insulated conductive wire. The electrode is used in a urological resectoscope having an axially extending shaft tube, the proximal end thereof being fixed to a main body. A sliding body is proximally positioned in relation to the main body, and can slide in a parallel manner in relation to the axis thereof. The sliding body includes a receiver into which the proximal end region of the electrode carrier can be introduced. The carrier penetrates the main body and is positioned such that it can slide axially in the shaft tube assembly position in order to fix a fixing section of the electrode carrier via a fixing device pertaining to the sliding body, and in order to contact a first contacting section of the electrode carrier via a first contacting device pertaining to the main body. The fixing section is proximally arranged in relation to the first contacting section.

10 Claims, 3 Drawing Sheets

MONOPOLAR AND BIPOLAR ELECTRODE FOR A UROLOGICAL RESECTOSCOPE

BACKGROUND OF THE INVENTION

1. Field of the Invention

The present invention relates to a monopolar and to a bipolar electrode for a urological resectoscope.

2. Description of Related Art

Resectoscopes are mostly used foremost for prostate resections, though, depending on the particular design, they also may be used for other surgical purposes. Herein the concept of "resectoscope" denotes endoscopic instruments wherein an optics and a monopolar or bipolar electrode-support, together with one or two distal electrodes, for instance a resecting and a neutral electrode configured in a stem tube. Further, the electrode support together with the electrodes are configured in an axially displaceable manner and are affixed at its proximal end to a resectoscope slide block with which it makes electric contact. The slide block is axially displaceable by manually driving a grip in order to axially displace the electrode.

During prostate resection, the resectoscope is advanced by its distal stem tube end through the urethra inside the prostrate. When hf is applied to the electrode, this electrode may be advanced and retracted by manually driving the slide block in order to cut tissue. Generally, the electrode is configured as a wire loop to trim tissue snippets. Furthermore, the electrode may assume other geometries, for instance being a button electrode, a roller electrode, a knife electrode or the like, in order to allow application to different purposes such as coagulation, cutting or the like.

Classical resectoscopy makes use of the monopolar or unipolar technology. Therein an hf current is set up between the resection electrode—the active electrode—through the patient's body and a neutral electrode of comparatively large surface externally affixed to the patient, for instance to his thigh.

However, the electric current through the patient's body entails risks that cannot be totally excluded even when the resectoscope is handled expertly. For instance, there are uncontrollable leakage or drift currents which, if the patient were to touch metal, for instance that of the operational table, may result in painful skin burns. Also, as regards current-induced muscle contractions, there is the danger the patient may move suddenly in an uncontrolled manner whereby he might be cut by the resectoscope. There is always some danger that muscles or nerves in the vicinity of the resection zone shall be damaged at least temporarily by drifting currents.

The above cited risks may be nearly entirely eliminated when using bipolar techniques. All such techniques offer the feature that not only the active electrode, but also the neutral or return electrode, are inserted into the body of the patient. As a result of this, the hf current is set up only between the two electrodes at the electrode support—but not, or merely over defined, short paths, through the body of the patient. Such a bipolar electrode is disclosed in the German Offenlegungsschrift 25 21 719 wherein, therefore, the electrode support is crossed by two electrical conductor wires.

It is also known, with respect to bipolar electrodes, to replace the neutral electrode with a second active electrode acting as the return electrode, the electric current being set up between these two electrodes each of which makes contact with the tissue. Such a bipolar electrode is shown in the patent document WO 96/234449.

However, both the monopolar and bipolar electrodes incur the problem of properly setting up electrical contact between the conductor wires feeding an electric current to the electrodes and their contact zones in the slide block. There the electrical connection or contact must be set up using extension cables leading to the output terminals of a separately set up hf generator. HF-loaded contact sites are problematical and tend to defects such as charring.

In older designs, a tightening screw simultaneously sets up the contact and the mechanical affixation of the electrode support inside the slide block. Once such a contact site chars, the entire slide block must be replaced.

A monopolar design of this kind is known from FIG. 3 of each of U.S. Pat. Nos. 4,917,621 and 4,919,131. The slide block is fitted with a continuous transverse cavity accepting the plug of the hf extension cable to contact the bared contact zone of the electrode support in this cavity. A clamping element acting on the affixation zone of the electrode support is configured distally relative to the cavity.

This design offers the advantage of separately mechanically affixing the electrode support and the clamping element on the slide block, as a result of which it is possible to first check this slide block's appropriate mechanical operation. Thereupon contact may be implemented with the plug. If the contact site should char, only the electrode support and the cable together with the plug need be changed. The clamping element and the slide block, on the other hand, remain intact because the clamping element is separate.

However, the known design of the above species has drawbacks. Because the affixation device is configured distally from the contacting element, the electrode support site where affixation takes place is crossed by the electric conductor connecting the contacting site to the active electrode. As a result the electrode support lacks mechanical strength in this region. The affixation device must allow for this lack of strength and, illustratively, may only operate with minute tightening forces. If affixation takes place by means of a slide block entering a groove and acting on the electrode support, then the groove may only be very shallow and consequently the reliability of affixation shall be considerably reduced.

The proximal end zone of the electrode support is constituted by the zone wherein affixation takes place and by the contacting zone. Therefore, these zones, namely the full end zone of the electrode support, are rigid and more resistant to bending than the remainder of the electrode support, which consists only of an inner conductor and an outer insulation. In resectoscopes, however, the electrode support typically will be configured tightly against the optics inside the stem tube, whereas, in the region of the slide block, the support and optics must be farther apart in order to subtend enough space for the contacting system and the affixation device. Therefore, the electrode support must be pivotably supported inside the main block in the manner indicated, for instance, in FIG. 13 of the patent document WO 96/234449. Since the main block is required to be of moderate length on technical grounds, substantial pivoting must take place over a short path. However, such pivoting motion is hampered by the considerable length of the rigid end region of the known electrode supports.

Moreover assembly may be defective if the electrode support was insufficiently inserted and thereupon was fixed in place and contacted.

With reference to FIG. 16 of the patent document WO 96/234449, which includes a bipolar electrode, the electrode support is fitted with two contact zones in the region of the slide block. An extension cable plug, which can be affixed to the slide block, sets up contact with both contact zones, which it furthermore clamps onto. This design does not provide a separate, special affixation element. Therefore, this design precludes affixing the electrode support to test mechanical operation before contacting takes place.

SUMMARY OF THE INVENTION

An objective of the present invention is to create an improved, monopolar or bipolar electrode of the above species, allowing to affix the electrode support in the slide block and to set up an electrical connection or contact with both steps being implemented in problem-free manner.

In accordance with the preset invention, the electrode support of the electrode is separate from the affixation zone and is configured proximally relative to the first contact zone. Accordingly, as regards the resectoscope's slide block, the affixation element must be proximal relative to the first contact element.

As a result of this design separation, the electrode support must be mechanically separately affixed by means of the affixation element on the slide block whereby its appropriate mechanical operation may be tested in a first step. Thereupon, a plug may be applied to set up electrical contact. If the contact zone should char, then only the electrode support jointly with the cable and plug need be exchanged. The clamping element and the slide block remain intact because the clamping block is now designed separately. This electrode design moreover offers the advantage that the affixation zone of the electrode support no longer is crossed by an inner conductor and consequently may be designed for high mechanical strength. A number of different highly reliable affixation methods may be used, for instance clamping by applying high clamping forces, locking into deep grooves or even locking by means of a pin through a transverse borehole in the electrode support. Furthermore, highly retentive snap-in connections may be used. Another advantage offered by the proximal configuration of the affixation zone is that, assuming proper affixation, the electrode support is entirely inserted. That is, the electrode support's contact zone is configured at the site of the contact element and, hence, electrical contacting can be set up. Lastly, the problem of pivoting the rigid end zone of the electrode support during insertion into the main block may be very effectively solved. The bending-resistant end piece consisting of the contact zone and the affixation zone may be shortened. The electrode support's affixation zone also may be designed with a lesser diameter, thereby enabling tighter pivoting.

In further accordance with the present invention, and with respect to a bipolar electrode, the affixation zone is configured apart from both contact zones and proximally to at least one of them. In this manner it is possible to first test the appropriate mechanical operation before setting up electrical contact by means of a plug.

The electrode of the present invention, on one hand, makes it possible to configure the first contact zone proximally and to mount the second one distally from the affixation zone. In corresponding manner, the affixation element should be configured between the two contact elements in the slide block. Advantageously, only one inner conductor would cross the affixation zone and thereby a higher clamping force might be applied to the affixation zone. This feature also would facilitate insulating the two contact zones because they already are being separated by the affixation zone when affixation zone is made of an insulating materials such as a non-conducting ceramic.

In further accordance with the present invention, two contact zones are configured distally relative to the affixation zone. In this case and with respect to the resectoscope's slide block, the affixation element is disposed proximally relative to the two contact devices. Such an electrode design offers the advantage in that neither inner conductor crosses the electrode support's affixation zone and, thus, the affixation zone may be designed for very high mechanical strength. In this manner the affixation advantages discussed hereinbefore with reference to a monopolar electrode can be achieved. Another advantage offered by the affixation zone's proximal configuration is that, assuming a proper affixation procedure, the electrode support is reliably fully inserted and, therefore, the electrode support's contact zones are also situated at the sites of the contact elements, whereby contacting free of defects may take place. Furthermore, the problem encountered with pivoting the stiff end segment of the electrode support during insertion through the main block can be very effectively solved. The bending-resistant end piece consisting of the two contact zones and of the affixation zone then may be shortened, however the insulation between the two contact zones must be preserved. The electrode support's affixation zone also may be designed to be of a lesser diameter, as a result of which guidance by a tighter pivoting motion is improved.

In further accordance with the present invention, the affixation zone is wholly separated from the remaining design of the electrode support in order to attain good affixation. A solid and continuous metal design may also be selected.

The affixation zone and at least part of an adjacent contact zone may be integral. As a result, the design is simplified with respect to manufacture and greater mechanical strength is attained. When both contact zones are situated distally from the affixation zone, then, according to the invention, at least the proximal part of the contact zone adjacent to the affixation zone shall be made integral, with the affixation zone. When the affixation zone is situated between the two contact zones, then selectively either the distal portion of the contact zone proximally adjacent to the affixation zone shall be integral with the affixation zone, or at least the proximal portion of the contact zone, which is distally adjacent to the affixation zone is integral with the affixation zone.

In further accordance with the invention, the affixation zone is made of an electrically insulating material if it is configured between the two contact zones. In that case the affixation zone contributes to insulated length and thereby allows shortening the electrode's proximal end.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
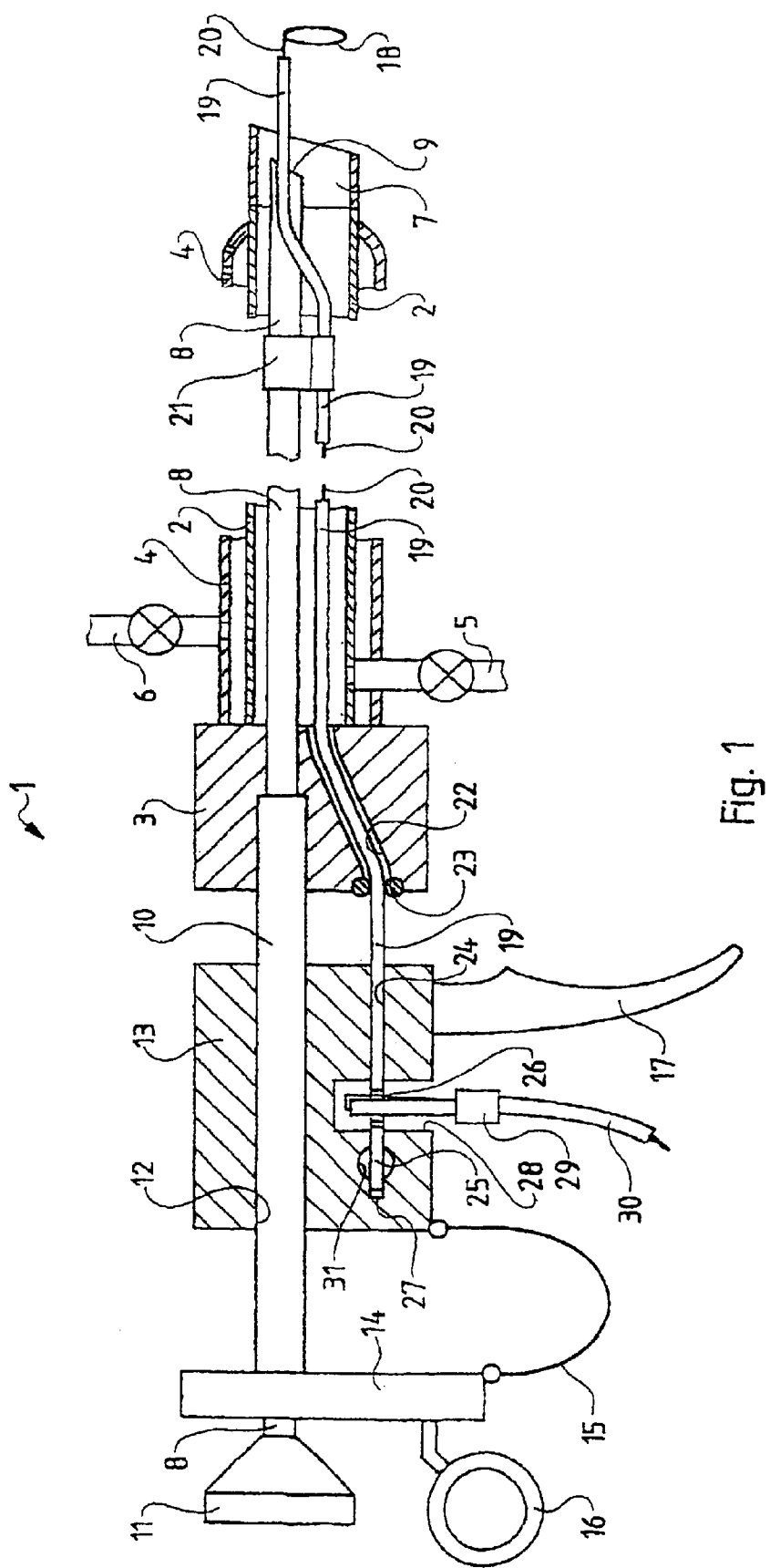
FIG. 1 is an axial section of a resectoscope and shows a first illustrative embodiment of an assembled monopolar electrode.

The resectoscope 1 shown in FIG. 1 comprises a stem tube 2, which is affixed by its proximal end to a main block 3. In manner not shown, the stem tube 2 may be detachably mounted by means of a conventional coupling to the main block 3. An external tube 4 encloses the stem tube 2 and also is affixed to the main block 3, again in conventional manner and by means of a coupling (not shown). The inside of the stem tube 2 serves as feed duct for permanent irrigation and, as shown by FIG. 1, is accessible externally through a valve-fitted hookup 5, which may be connected to a hose. Another identical hookup 6 to connect another hose is connected to the annular gap between the stem tube 2 and the external tube 4 acting as the return duct.

The two tubes 2 and 4 are conventionally metallic. The distal end zone of the stem tube 2 is conventionally insulating and illustratively in the form of a ceramic element 7.

An optics 8 runs axially inside the stem tube 2 and, in the shown assembled configuration, views by its distal objective 9 the field of surgery ahead of the ceramic end element 7, while proximally it runs through the main block 3. From the latter position it runs through a guide tube 10 affixed in the main block 3 and terminates on the other side of the proximal end of the tube 10 into an ocular 11 that may be replaced by a camera.

By means of a guide borehole 12, a slide block 13 rests in an axially displaceable manner on the guide tube 10. An end plate 14 is affixed to the proximal end of the guide tube 10 and by means of a conventional leaf spring 15 resiliently braces the slide block 13. A thumb ring 16 is mounted on the end plate 14, and a finger grip 17 is mounted on the slide block 13. Using one hand, the surgeon by means of the thumb and index finger can actuate the thumb ring 16 and the finger grip 17 and thus may axially displace the slide block 13. Alternatively, the just discussed "active" function may be replaced by a "passive" function wherein the leaf spring 15 is configured between the slide block 13 and the main block 3 and the drive sites 16, 17 also are situated at these components.

The shown resectoscope includes an exchangeable, hf-loaded, monopolar electrode 18 that is of conventional design with respect to prostate resection. Namely, the electrode 18 is in the form of a wire loop of which the plane is orthogonal to the axial direction. The electrode 18 is supported by an electrode support 19 in the form of an inner conducting wire 20 enclosed by an external insulation. In conventional manner, this electrode support 19 rests by means of a sleeve 21 in a longitudinally displaceable manner on the optics 8 and runs through the stem tube 2 as far as the main block 3. From the main block the electrode support 19 runs through a laterally deviated transmission duct 22 fitted with O rings 23 or the like to seal off the liquids, and then extends from the duct's proximal mouth again parallel to the axis, but at a larger distance from the axis, into a seating borehole 24 in the slide block 13. In an alternative embodiment, the seating borehole 24 may be replaced, for instance, by a proximally conically converging aperture, or a sideways open slot, or the like, to seat the electrode support 19.

In its proximal end region, the electrode support 19 comprises an affixation zone 25 constituting its end element, the end zone 25 being appropriately mechanically strong, for instance being made of solid metal in order to allow reliably mechanically affixing the electrode support at that site. Distally from there, the electrode support 19 adjoins a contact zone 26 fitted with an electrically conducting outside surface that is connected in an electrically conducting manner with the conducting wire 20 of the electrode support 19.

In the form of its proximal end 27, the seating borehole 24 further comprises a limit stop for the electrode support 19 that can be inserted in the proximal direction into the seating borehole 24 as far as the stop.

When, in the shown assembly, the electrode support 19 has been inserted in the seating borehole 24 of the slide block 13 as far as the limit stop 27, then it shall be situated with its contact zone 26 in a clearance 28 of the slide block 13 wherein the contact zone 26 is freely accessible from the outside. In that configuration, the electrode support 19 may be electrically contacted, for instance, by the shown clamping plug 29 at the end of a cable 30 running to an hf generator (not shown).

An affixation element, which in this embodiment comprises a transverse borehole 31, is configured directly proximally next to the clearance 28 in the region of the affixation zone 25 of the electrode support 19 in the slide block 13 and illustratively is fitted with an inside thread to allow a tightening screw to be screwed in. Alternatively, the affixation element also may be of another design, for instance including a slider engaging a groove, or in the form of a snap-in connection or the like.

As shown, the clearance 28 may offer omnidirectional, free access to the contact zone 26 of the electrode support 19, however, and in illustrative manner, it may also be designed as a cavity accessible only from one side as disclosed for, instance, in U.S. Pat. No. 4,919,131.

Once the electrode support 19 is appropriately affixed in the slide block 13 and appropriate electrical contact is made, then, by means of the above displacement of the slide block 13, the entire electrode support 19 together with the electrode 18 may be displaced longitudinally relative to the stem tube 2. Thereupon, by observation through the optics 8 and applying hf to the electrodes 18 and 118, the electrode may be used for cutting while moving axially.

The clamping plug 29 will be removed and the affixation element (transverse borehole 31) will be loosened when the electrode support 19 must be exchanged. Thereupon, the electrode support may be fully extracted in the distal direction from the resectoscope 1. In the same way, a new electrode may be inserted in the proximal direction as far as the limit stop 27, then mechanically affixed and electrically contacted. The electrode support 19 may be first mechanically affixed to the transverse borehole 31 and its appropriate mechanical operation may be tested by displacing the slide block 13 to and fro before electric contact is implemented with the clamping plug 29.

Figure 2:
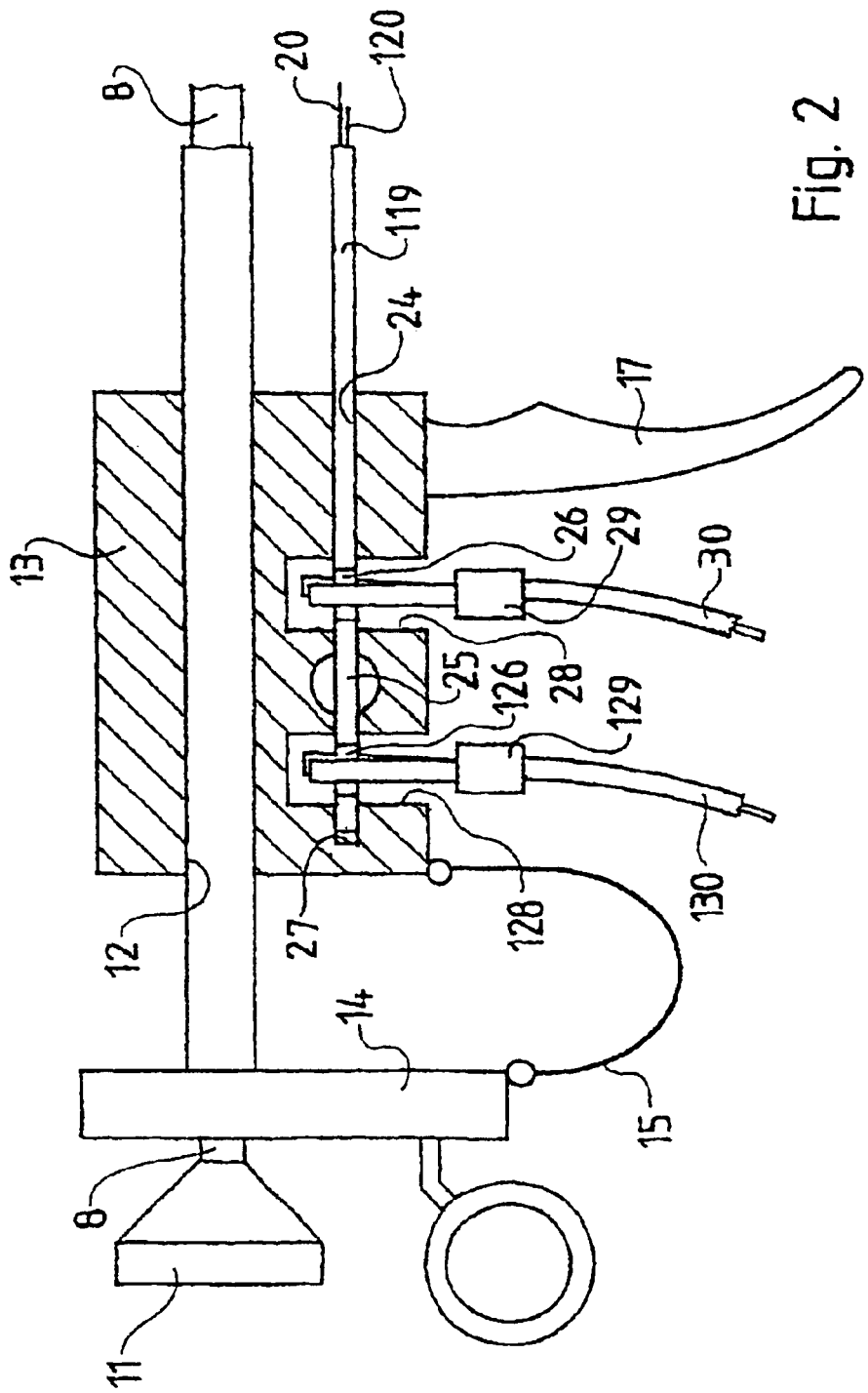
FIG. 2 is an axial section of the proximal end of a resectoscope and shows a first illustrative embodiment of an assembled bipolar electrode.
Figure 3:
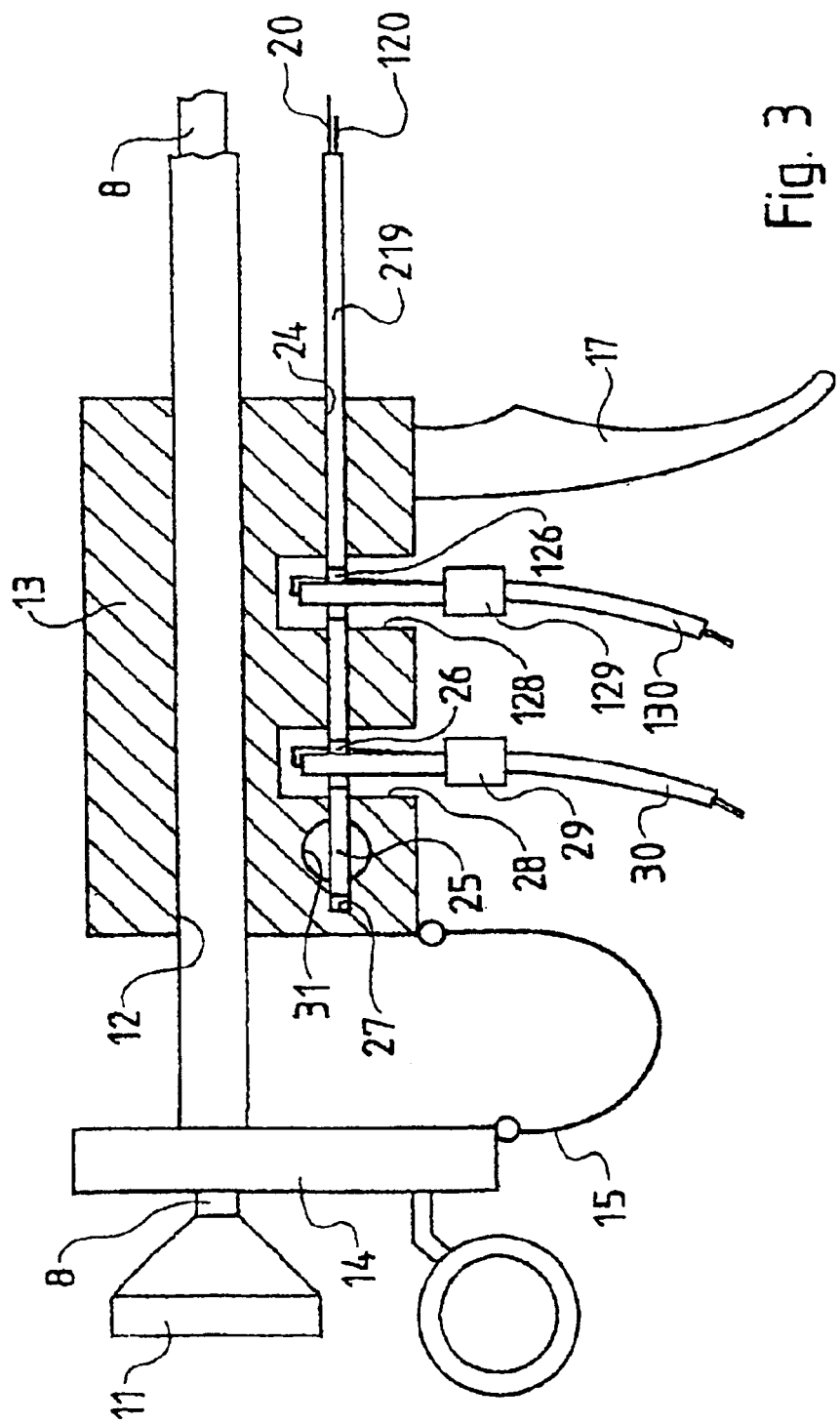
FIG. 3 is an axial section of the proximal end of a resectoscope and shows a second illustrative embodiment of an assembled bipolar electrode.

FIGS. 2 and 3 show two mutually alternative bipolar electrodes of the invention in their assembled state, identical elements as in FIG. 1 being denoted here identically too. Examples of representative bipolar electrodes are disclosed in the German patent document 100 28 850.2 and in the documents cited therein. Therefore, the distal regions of the bipolar electrodes are not shown in FIGS. 2 and 3.

FIG. 2 shows two electrically conducting wires 20 and 120 inside the insulating electrode support 119 and running distally as far as the active and the return electrodes and connecting the electrodes in an electrically conducting manner with a first and a second contact zone 26 and 126, which are just as much insulated from each other as are the conducting wires 20 and 120 and which may be connected, for instance, using a double plug. Similar to the embodiment shown herein, it is also possible to conductively connect the return electrode with the first contact zone and the active electrode with the second contact zone.

The electrode support 119 comprises an affixation zone 25 between the two contact zones 26 and 126. The affixation zone 25 is designed to be mechanically strong enough to reliably mechanically affix the electrode support 119 at the affixation zone 25. Illustratively the affixation zone 25 may consist of an insulating material of adequate mechanical strength. As before, the electrode support 119 comprises a nearby first contact zone 26 that is fitted with an electrically conducting outside surface that in turn is connected in an electrically conducting manner with the conductorwire 20 of the electrode support 119.

The electrode support 119 furthermore is fitted proximally from the affixation zone 25 with a second contact zone 126 that also comprises an electrically conducting outside surface that in turn is connected in electrically conducting manner with the second conductor wire 120 of the electrode support 119.

In the manner already shown in relation to FIG. 1, the seating borehole 24 by means of its proximal end 27 comprises a limit stop for the electrode support 119, and the support may be inserted in the proximal direction-through the seating borehole 24 as far as the stop.

If, in the shown assembly configuration, the electrode support 119 was inserted as far as the limit stop 27 into the seating borehole 24, of the slide block 13, then it will be situated by its contact zone 26 in a clearance 28 in the slide block 13 where the contact zone 26 is freely accessible from the outside. At the same time the electrode support is situated by its contact zone 126 in a second clearance 128 of the slide block 13 where this second contact zone 126 is freely externally accessible. Both contact zones may be electrically connected at the sites, for instance by means of the shown clamping plugs 29 and 129, to the ends of cables 30 and 130 leading to the output of an hf generator (not shown). Such electrical connection, i.e. contacting, also may be implemented using a double plug which simultaneously implements electrical connection to the two contact zones 26 and 126.

Lastly FIG. 3 shows a second and exchangeable hf-loaded bipolar electrode support 219 in the form of inner conductor wires 20 and 120 enclosed by insulation. The electrode support 219 at its proximal end comprises an affixation zone 25 constituting its end piece and being sufficiently strong mechanically, for instance being of solid metal, to reliably mechanically secure the electrode support 19 in that place. Distally adjoining it, the electrode support 219 comprises, as before, a first contact zone 26 fitted with an electrically conducting outside surface that is connected in an electrically conducting manner with the conductor wire 20 of the electrode support 219. A second contact zone 126 follows distally away from the first contact zone 26 and is insulated from it and also is fitted with an electrically conducting outside surface which in turn is connected in electrically conducting manner with the conductor wire 120 of the electrode support 219.

When, in the shown assembled configuration, the electrode support 219 has been inserted as far as the limit stop 27 in the seating borehole 24 of the slide block 13, then it will be situated by its first contact zone 26 in a clearance 28 of the slide block 13 wherein the contact zone 26 is freely accessible from the outside. At the same time its second contact zone 126 is situated in a second clearance 128 of the slide block 13 wherein the contact zone 126 is freely accessible. Both of the contact zones in the clearances 28, 128 may be electrically connected, for instance, by means of the shown two clamping plugs 29 and 129 positioned at the ends of the extension cables 30 and 130, which run to the two output terminals of an omitted hf generator.

An affixation element corresponding to that described above in relation to FIG. 1 is configured in the slide block 13 directly proximally next to the first clearance 28 in the region of the affixation zone 25 of the electrode support 219.

As shown, the clearances 28 and 128 may provide free and omnidirectional access to the contact zones 26 and 126 of the electrode support 219, or illustratively they may be configured as cavities that are accessible only from one side, for instance in the manner disclosed in U.S. Pat. No. 4,919,131.

In order to exchange the electrode support 219, the clamping plugs 29 and 129 are removed and the affixation element (transverse borehole 31) is loosened. Thereupon, the electrode support 219 may be fully extracted in the distal direction from the resectoscope 1. Reversely a new electrode may be inserted in the proximal direction as far as the limit stop 27 and mechanically secured and electrically connected by contacting. This design allows first to mechanically secure the electrode support 19 in the transverse borehole 31 and to test appropriate mechanical operation by moving the slide block 13 to-and-fro before electrical connection is implemented by means of the clamping plugs 29 and 129.

Instead of the embodiments shown herein, the electrode 18 also may assume other geometries, for instance being in the form of a button electrode, a pin electrode, a roller electrode or a knife electrode, which, upon being loaded with hf, shall function in a coagulating, vaporizing or cutting manner. In the case of bipolar electrodes, one of the electrodes may be designed as the neutral electrode that will not touch any tissue, whereas the other electrode will constitute the active electrode. Just as well, however, both electrodes may touch the tissue and function simultaneously for instance in coagulating and resecting manner.

In all the above embodiments of FIGS. 1 through 3, the limit stop relating to the insertion of the electrode support 19, 119 or 219 always is the end 27 of the seating borehole 24. However, a limit stop also may be configured at the affixation element itself, for instance at the tightening screw rotating inside the threaded borehole 31. If, for instance, a slider is used as a clamping element and enters a groove in the affixation zone 25, then an appropriate stop also may be configured at the slider, the stop cooperating in appropriate manner for instance with a corresponding stop on the affixation zone 25.

The above embodiments show that the properly mounted electrode support 19, 119 or 219 by means of its contact zones 26 and 126 is configured in the slide block 13 in clearances 28 and 128 so as to be freely accessible from the outside in order that, as shown, the contact zones may be electrically contacted using, as shown, plugs 29 or 129 inserted from the outside, said plugs optionally also being a double plug. However, other contact devices also are applicable, such as where the contact zone 26 makes an electric connection with a terminal affixed to the slide block 13, for instance inside the latter, and an extension cable running from the block in a manner other than shown. In that case the clearance 28 may be eliminated. The same considerations apply to the second contact zone 126 and the second clearance 128.

In the above shown embodiments, the affixation zone 25 and the contact zones 26 and 126 are shown being separate. However, one of the contact zones also may be integral with the affixation zone, for instance the contact zone 26 in FIGS. 1, 2 and 3 or the contact zone 126 in FIG. 2.

As regards such an integral design of affixation zone and contact zone, the former manifestly shall be at an electrical potential. This feature however fails to be a drawback because the slide block 13 generally is made of an insulating material and the affixation element 31 also may be very easily designed to be electrically insulating relative to the outside.

What is claimed is:

1. An HF-loaded electrode (18) cooperating with an electrode support (19, 119, 219) consisting of at least one externally insulated electric conductor wire (20, 120) for use in a urological resectoscope (1) comprising a stem tube (2) running in an axial direction and affixed at a proximal end to a main block (3), a slide block (13) being supported proximally from said main block and in an axially displaceable manner parallel to said main block, said slide block comprising a seat (24) into which, when said resectoscope is assembled, is inserted a proximal end region of the electrode support (19, 119, 219), the electrode support resting and axially displaceable in the stem tube (2) and crossing the main block (3) in order to affix an affixation zone (25) of the electrode support (19, 119, 219) via an affixation element (31) of the slide block (13) and to electrically contact a first contacting zone (26, 126) of the electrode support (19, 119, 219) via a first contacting element (28, 29, 128, 129) of the main block (3), wherein the affixation zone (25) is configured proximally relative to the first contact zone (26, 126).

2. The hf-loaded electrode (18) as claimed in claim 1, wherein the electrode support (119, 219) comprises two electric conductor wires (20, 120) and two contact zones (26, 126) that cooperate with said two conductor wires.

3. The hf-loaded electrode as claimed in claim 2, wherein the affixation zone (25) is configured proximally relative to the two contact zones (26, 126).

4. The hf-loaded electrode as claimed in claim 1, wherein the affixation zone (25) deviates from a remaining cross-section of the electrode support (19, 119, 219).

5. The hf-loaded electrode as claimed in claim 1, wherein the affixation zone (25) consists of solid metal.

6. The hf-loaded electrode as claimed in claim 1, wherein the affixation zone (25) and at least a portion of an adjacent contact zone (26, 126) are integral.

7. The hf-loaded electrode as claimed in claim 2, wherein the affixation zone (25) is configured between the contact zones (26, 126) and consists of an insulating material.

8. The hf-loaded electrode as claimed in claim 2, wherein the affixation zone (25) deviates from a remaining cross-section of the electrode support (19, 119, 219).

9. The hf-loaded electrode as claimed in claim 2, wherein the affixation (25) consists of solid metal.

10. The hf-loaded electrode as claimed in claim 2, wherein the affixation zone (25) and at least a portion of an adjacent contact zone (26, 126) are intergral.

* * * * *